United States Patent [19]
Van Os et al.

[11] 3,952,734
[45] Apr. 27, 1976

[54] INTRA-UTERINE-DEVICE

[75] Inventors: Willem Arthur Adriann Algernon Van Os, Aerdenhout; Pieter Eduard Reinier Rhemrev, Heemstede, both of Netherlands

[73] Assignee: Multilan S.A., Fribourg, Switzerland

[22] Filed: Feb. 6, 1975

[21] Appl. No.: 547,657

[30] Foreign Application Priority Data
Feb. 14, 1974 Netherland................... 7402008

[52] U.S. Cl................................ 128/130; 128/260
[51] Int. Cl.²......................................... A61F 5/46
[58] Field of Search..................... 128/127, 130, 260

[56] References Cited
UNITED STATES PATENTS

| | | | |
|---|---|---|---|
| 3,533,406 | 10/1970 | Tatum................................. | 128/130 |
| 3,782,376 | 1/1974 | Lerner................................. | 128/130 |
| 3,820,535 | 6/1974 | Marco................................. | 128/130 |
| 3,857,391 | 12/1974 | Lerner................................. | 128/127 |
| 3,880,156 | 4/1975 | Hoff................................... | 128/130 |

OTHER PUBLICATIONS
IUD Devices — MIT — Jan. 1971 p. 29.

*Primary Examiner*—Lawrence W. Trapp
*Attorney, Agent, or Firm*—Lane, Aitken, Dunner & Ziems

[57] ABSTRACT

Intra-uterine-device meant to be inserted into the uterus, comprising an elongated stem, carrying at one end two resilient, canti-levered arms, extending sideways on either side of the stem, which stem is contained within a tube shaped sheath by means of which the device may be inserted into the uterine cavity through the cervix, after which the sheath may be pulled back, wherein the sheath narrowly encloses the stem, whereas the shape and flexibility of the arms are chosen in such manner, that the arms are easily collapsable onto the outer surface of the sheath. The arms, when relaxed, curve back towards the stem, so that they substantially form part of an ellipse, the longer axis of which coincides with the stem. The stem may at least partially be covered with a layer preventing pregnancy, which layer enhances the effect of the device. This layer may consist of a copper wire wound on the stem or of a carrier for a hormone preparation.

5 Claims, 2 Drawing Figures

INTRA-UTERINE-DEVICE

The invention relates to an intra-uterine device intended to be inserted into the uterus, comprising an elongated stem carrying at one end two elastic cantilevered arms extending sideways on either side of the stem, the stem being contained within a tube shaped sheath, by means of which the device may be inserted into the uterine cavity through the cervix, after which the sheath may be pulled back.

The known devices of this type, which are meant to be inserted into the uterus, are in most cases resiliently collapsable in such manner, that they may pass through the very narrow cervix before they relax to the necessary size within the uterine cavity.

One known device of this kind has arms which may be pushed into the sheath while they are collapsed, after which the sheath may be inserted into the cervix. Thereafter the device may be pushed out of the sheath into the uterine cavity by means of a pushing rod, so that the arms are allowed to spread themselves. Finally the sheath and the rod are pulled back. This device has the disadvantage that the sheath must have a relatively large diameter in order to be able to receive the collapsed arms, so that the sheath can only be inserted into the cervix with some difficulty and as a rule not without causing pain. Apart from that, the arms loose their so called elastic memory when they are held collapsed for some time, so that the arms can only be pushed into the sheath immediately before use by means of the rod, which makes an additional step necessary and may be undesirable from a hygienic point of view.

The invention has as an object to remove the foregoing disadvantages.

According to the invention this object is realised with a device of the kind described, because the sheath narrowly encircles the stem and because the shape and the flexibility of the arms are choosen in such manner that the arms are easily collapsable onto the outer surface of the sheath.

Preferably the arms are curved back towards the stem when relaxed, so that they describe a part of an ellipse, the longer axis of which coincides with the stem.

Because the arms of the device according to the invention do not have to be accomodated within the sheath, the diameter of the sheath may be relatively small. As the arms are easily collapsable onto the outer surface of the sheath they are automatically folded together when the device is inserted into the cervix. Thus the overall diameter of the device in collapsed state, including the sheath, may be smaller than in the case where the arms have to be accomodated within the sheath. As soon as the collapsed arms have passed the cervice, they spread out within the uterine cavity, after which the sheath may be pulled back, whereas the device itself is held within the uterine cavity by means of small protuberances formed on the arms. Because the arms always lie outside of the sheath and are not pressing against the inner surface of the sheath, an auxillary means in the shape of a rod for pushing the stem out of the sheath is not necessary.

In order to enhance the function of the device it is advantageous to, at least partially, cover the stem with a layer which prevents pregnancy.

This layer may comprise a metal as for instance a copper wire wound on the stem, or a carrier for a hormone preparation.

The invention will be further explained with reference to the drawings showing an embodiment of the invention.

Figure 1:
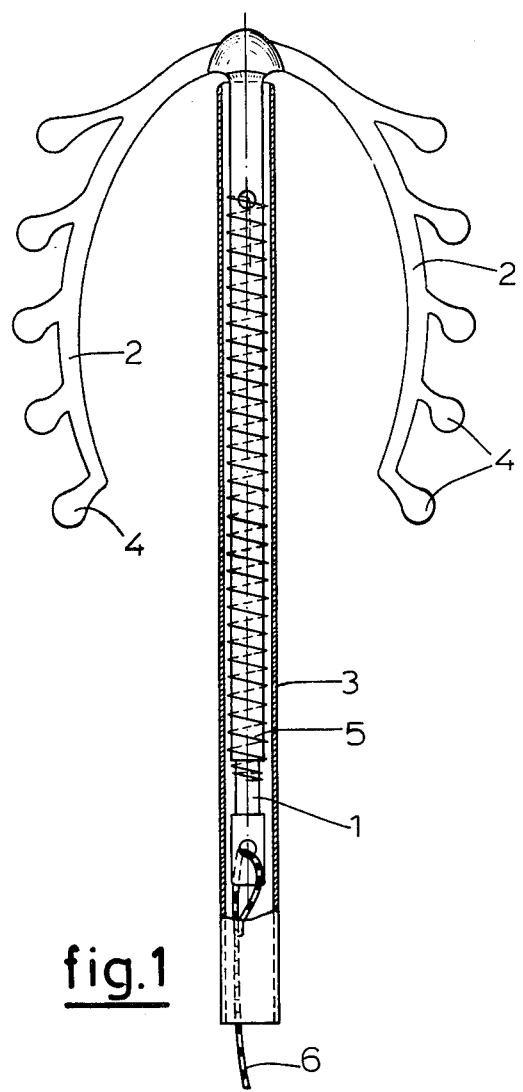
FIG. 1 is a view of a device according to the invention, partially in section taken along the line I—I in FIG. 2.
Figure 2:
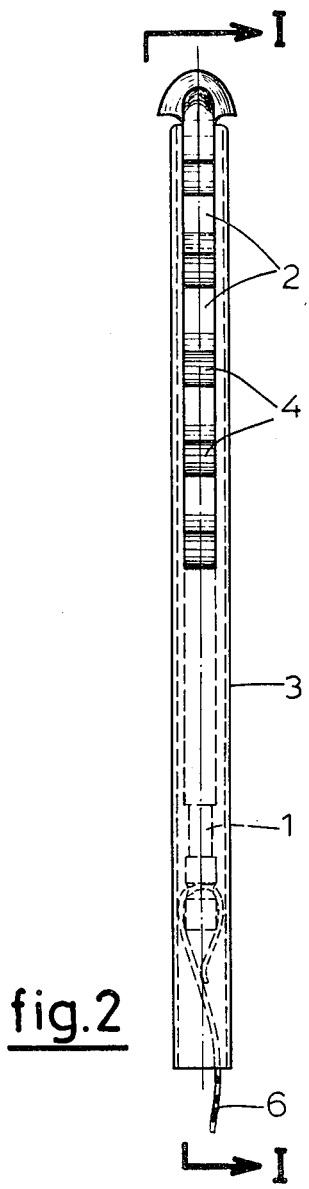
FIG. 2 is a side-view of the device shown in FIG. 1.

The intra-uterine-device shown in the drawing comprises an elongated stem 1, which carries at one end two elastic cantilever arms 2, which arms extend sideways on either side of the stem 1. The arms, when relaxed as depicted in FIG. 1, curve back towards the stem 1, so that they substantially describe part of an ellipse, the longer axis of which coincides with the stem 1. The stem 1 is contained within a tube shaped sheath 3 with little play, by means of which the device may be inserted into the uterus.

Because the device must be brought into the uterine cavity through the very narrow cervix, the arms 2 may easily be folded together onto the outer surface of the sheath 3. Thanks to the great resilience and the curved shape of the arms 2, the arms are automatically collapsed when the stem is inserted into the cervix by means of the sheath 3. After the arms have passed the cervix they are enabled to resiliently spread themselves again, after which the sheath 3 may be pulled back, whereas the device itself is held within the uterine cavity by means of small protuberances 4 provided on the outerside of the arms 2.

In order to enhance the function of the device the stem may be covered with a layer which prevents pregnancy. This layer may be metallic as for instance a copper wire 5 wound on the stem 1 as shown in FIG. 1. The layer may also consist of a carrier for a hormone preparation. In order to be able to remove the device from the uterus when desired, a pulling wire 6 is attached to the free lower end of the stem 1, said wire protruding from the cervix.

In order to prevent the upper edge of the sheath 3 from causing pain when the device is inserted through the cervix, the upper end of the stem 1, which carries the arms 2 is provided with a rounded head 7, which overlaps the upper edge of the sheath 3.

Because the device does not aggressively expand within the uterine cavity, unlike the known devices, the device according to the invention causes little or no bleedings or cramps. Therefore and also because the device is self seeking the expulsion rate of the device according to the invention is extremely low as compared with known devices of the same general type.

We claim:

1. Intra-uterine-device meant to be inserted into the uterus, comprising an elongated stem, carrying at one end two resilient, canti-levered arms, extending sideways on either side of the stem, which stem is contained within a tube shaped sheath by means of which the device may be inserted into the uterine cavity through the cervix, after which the sheath may be pulled back, characterized in that, the sheath narrowly encloses the stem, whereas the shape and flexibility of the arms are choosen in such manner that the arms, when passing the cervix, are pressed together onto the outer surface of the sheath by the cervix wall, said arms, when relaxed after insertion, curving back towards said stem so that they substantially form a portion of an ellipse, the longer axis of which coincides with said stem.

2. Device according to claim 1, characterized in, that the stem is at least partially covered with a layer preventing pregnancy, which layer enhances the effect of the device.

3. Device according to claim 2, characterized in that the layer consists of metal and more particularly of a copper wire wound on the stem.

4. Device according to claim 2, characterized in that the layer consists of a carrier for a hormone preparation.

5. Device according to claim 1 wherein said one end of said stem is formed into a curved head portion to facilitate said insertion of said device.

* * * * *